United States Patent
Endo et al.

(10) Patent No.: US 8,730,465 B2
(45) Date of Patent: May 20, 2014

(54) POLARIZED LIGHT DEFECT DETECTION IN PUPIL IMAGES

(75) Inventors: Kazumasa Endo, Kawasaki (JP); Daisaku Mochida, Nagoya (JP); Toru Yoshikawa, Yokohama (JP); Hiromasa Shibata, Yokohama (JP); Akitoshi Kawai, Yokohama (JP)

(73) Assignee: Nikon Corporation, Tokyo (JP)

( * ) Notice: Subject to any disclaimer, the term of this patent is extended or adjusted under 35 U.S.C. 154(b) by 310 days.

(21) Appl. No.: 12/314,995

(22) Filed: Dec. 19, 2008

(65) Prior Publication Data

US 2009/0147247 A1  Jun. 11, 2009

Related U.S. Application Data

(63) Continuation of application No. PCT/JP2007/064764, filed on Jul. 27, 2007.

(30) Foreign Application Priority Data

Aug. 2, 2006 (JP) .................................. 2006-211075
May 22, 2007 (JP) .................................. 2007-134968

(51) Int. Cl.
*G01N 21/88* (2006.01)

(52) U.S. Cl.
USPC .................... 356/237.4; 356/369; 356/426

(58) Field of Classification Search
None
See application file for complete search history.

(56) References Cited

U.S. PATENT DOCUMENTS

| 6,512,578 B1* | 1/2003 | Komatsu et al. ............ 356/237.5 |
| 6,690,469 B1 | 2/2004 | Shibata et al. |
| 7,480,050 B2* | 1/2009 | Den Boef et al. ............. 356/364 |
| 2002/0118359 A1* | 8/2002 | Fairley et al. ............... 356/237.2 |
| 2003/0020904 A1* | 1/2003 | Uto et al. .................... 356/237.2 |
| 2003/0053046 A1* | 3/2003 | Ise et al. ..................... 356/237.2 |
| 2004/0207836 A1* | 10/2004 | Chhibber et al. .......... 356/237.4 |

(Continued)

FOREIGN PATENT DOCUMENTS

| CN | 1087424 A | 6/1994 |
| JP | A-02-189448 | 7/1990 |

(Continued)

OTHER PUBLICATIONS

Office Action issued in Chinese Patent Application No. 200780026859.8 on Aug. 9, 2010 (with English Translation).

(Continued)

*Primary Examiner* — Gregory J Toatley
*Assistant Examiner* — Rebecca C Bryant
(74) *Attorney, Agent, or Firm* — Oliff & Berridge, PLC

(57) ABSTRACT

A defect inspecting apparatus inspects defects of a sample having a pattern formed on the surface. The defect inspecting apparatus is provided with a stage which has a sample placed thereon and linearly moves and turns; a light source; an illuminating optical system, which selects a discretionary wavelength region from the light source and epi-illuminates the sample surface through a polarizer and an objective lens; a detecting optical system, which obtains a pupil image, by passing through reflection light applied by the illuminating optical system from the surface of the sample through the objective lens and an analyzer which satisfies the cross-nichols conditions with the polarizer; and a detecting section which detects defects of the sample by comparing the obtained pupil image with a previously stored pupil image. Conformity of the pattern on a substrate to be inspected can be judged in a short time.

19 Claims, 15 Drawing Sheets

(56) References Cited

U.S. PATENT DOCUMENTS

| | | |
|---|---|---|
| 2005/0280806 A1 | 12/2005 | Oomori et al. |
| 2007/0070336 A1* | 3/2007 | Maeda et al. ............... 356/237.2 |
| 2007/0229833 A1* | 10/2007 | Rosencwaig et al. ......... 356/426 |
| 2007/0247616 A1* | 10/2007 | Hamamatsu et al. ...... 356/237.1 |

FOREIGN PATENT DOCUMENTS

| | | |
|---|---|---|
| JP | A-08-162511 | 6/1996 |
| JP | A-2000-155099 | 6/2000 |
| JP | A-2005-188944 | 7/2005 |
| WO | WO 94/08229 | 4/1994 |

OTHER PUBLICATIONS

Pluta, M., "Advanced Light Microscopy," 1988, title page and pp. 120, 121, 306-311, 316, 317, 334-337, vol. 1, Elsevier and Polish Scientific Publishers.

"Advanced Light Microscopy", Maksymilian Pluta, Polish Scientific Publishers, vol. 1, pp. 305-311, 316-317, 120-121 and 334-337. 1988.

Office Action issued Aug. 30, 2012 issued in Taiwanese Patent Application No. 96128167 (with partial translation).

* cited by examiner (a)

(b)

POLARIZED LIGHT DEFECT DETECTION IN PUPIL IMAGES

TECHNICAL FIELD

The present invention relates to a defect detecting apparatus and a defect detecting method.

BACKGROUND ART

In order to determine quality of a pattern formed on a surface of a semiconductor wafer, there are proposed various methods in which a sectional shape is measured by observation with Scanning Electron Microscope (SEM). In the observation of the sectional shape with SEM, the pattern on an inspected substrate is scanned in a sectional direction of the pattern with an electron beam, reflection electrons or secondary electrons from the pattern are detected and analyzed to obtain the sectional shape of the scanned portion. The operation is performed for several points on the pattern to determine the quality of the pattern shape as a whole.

As another method for determining the quality of the pattern an in-line measurement technique of measuring CD or an overlay with a scatterometer can also be cited.

In a spectral scatterometer, a scattered-light characteristic is measured at a fixed angle as a function of a wavelength, and usually a broadband light source such as a xenon lamp, a deuterium lamp, and a halogen-system light source such as a xenon-arc lamp is used. Either perpendicular incidence or oblique incidence may be used as the fixed angle.

In an angle-resolved scatterometer, the scattered-light characteristic is measured at a fixed wavelength as a function of an incident angle, and usually a laser beam is used as a single-wavelength light source.

Patent Document 1: Japanese Patent Publication Laid-Open No. 2005-188944

In the measurement method with SEM, because operations of irradiating and scanning the pattern with electron beam are repeatedly performed many times, a huge amount of time is required to obtain the pattern shape. All the pattern shapes on the wafer are hardly obtained due to high observation magnification, and some points are sampled to determine the quality of the whole wafer. As a result, a defect is overlooked if the defect is located in a portion except for the sample patterns. When a resist pattern is irradiated with electron beam, the resist absorbs the electron beam by an acceleration voltage, and the resist is charged up to generate deterioration of the pattern. In some cases, a discharge is generated to bring down the pattern, and inconvenience is generated in subsequent processes. Therefore, an optimum observation condition is obtained while the acceleration voltage or the observation magnification is changed in various ways. Thus, additional time is required for measurement.

One of problems of the angle-resolved scatterometer technique is that only one wavelength is detected in each time. Accordingly, when the spectrum has plural wavelengths, it is necessary to perform time-division multiplex of the wavelength, which increases the total time necessary to detect and process the spectrum. In the spectral scatterometer, it is necessary that a small grating be illuminated by light with small spread of incident angle, which wastes a large amount of light from the diffuse light source. Accordingly, a light level is decreased on a detector to lengthen the obtaining time, which adversely affects throughput. When a short obtaining time is selected, sometimes measurement result becomes unstable.

In view of the foregoing, a problem of the present invention is to provide surface inspecting apparatus and a surface inspecting method which can make a distinction between the acceptable and defective pattern shapes on the inspected substrate in a short time irrespective of a resist pattern and a post-etching pattern.

DISCLOSURE OF THE INVENTION

In accordance with a first aspect of the present invention, a defect inspecting apparatus which inspects a defect in a sample, a pattern being formed in a sample surface, is proposed. The defect inspecting apparatus includes a stage on which the sample is placed; a light source; an illumination optical system for epi-illumination of the sample surface with light emitted from the light source and transmitted through a polarizer and an objective lens; a detection optical system which detects a pupil image of the objective lens formed with the light of illumination reflected from the sample surface and transmitted through the objective lens and an analyzer, the analyzer satisfying a cross-nichols condition along with the polarizer; and a detecting unit which compares the obtained pupil image to a previously-stored pupil image to detect the defect in the sample.

In accordance with a second aspect of the present invention, a defect inspecting apparatus which inspects a defect in a sample, a pattern being formed in a sample surface, is proposed. The defect inspecting apparatus includes a stage on which the sample is placed; a light source; an illumination optical system for epi-illumination of the sample surface with light emitted from the light source and transmitted through a polarizer and an objective lens; a detection optical system which detects a pupil image of the objective lens formed with the light of illumination reflected from the sample surface and transmitted through the objective lens and an analyzer, the analyzer satisfying a cross-nichols condition along with the polarizer; and a detecting unit which compares portions of the pupil image to each other to detect the defect in the sample, the portions being symmetrical in relation to an optical axis.

In accordance with a third aspect of the present invention, in the defect inspecting apparatus of one of the first and second aspects, the illumination optical system includes an illuminance homogenizing unit; a plurality of interference filters which can select an arbitrary wavelength band; and an aperture stop, and illumination σ for the objective lens is variable.

In accordance with a fourth aspect of the present invention, in the defect inspecting apparatus of one of the first to third aspects, a rotation amount of polarization principal axis of the objective lens ranges from 1° to 25°.

In accordance with a fifth aspect of the present invention, in the defect inspecting apparatus of one of the first to fourth aspects, one of the polarizer and the analyzer includes a rotating mechanism, and instead of the cross-nichols relationship between the polarizer and the analyzer, an angle formed between a transmission axis of the polarizer and a transmission axis of the analyzer is set within a range of 65° to 89° by rotating one of the polarizer and the analyzer about an optical axis thereof.

In accordance with a sixth aspect of the present invention, in the defect inspecting apparatus of one of the first to fifth aspects, a high-sensitive point is adopted in the pupil image when the detecting unit detects the defect in the sample.

In accordance with a seventh aspect of the present invention, in the defect inspecting apparatus of one of the first to sixth aspects, a plurality of kinds of aperture stops are provided in the illumination optical system such that one of the plurality of kinds of aperture stops can be selected for use.

In accordance with an eighth aspect of the present invention, a defect inspecting method for inspecting a defect in a sample, a pattern being formed in a sample surface, is proposed. The defect inspecting method includes epiilluminating the sample surface with light emitted from the light source and transmitted through a polarizer and an objective lens; obtaining a pupil image of the objective lens with the light of illumination reflected from the sample surface and transmitted through the objective lens and an analyzer, the analyzer satisfying a cross-nichols condition along with the polarizer; and comparing the obtained pupil image to a previously-stored pupil image to detect the defect in the sample.

In accordance with a ninth aspect of the present invention, in the defect inspecting method of the eighth aspect, a repetition direction of the pattern is set to a direction shifted by 45° from a direction of the polarizer.

In accordance with a tenth aspect of the present invention, in the defect inspecting method of the eighth aspect, a repetition direction of the pattern is set to a direction shifted by 22.5° or 67.5° from a direction of the polarizer.

In accordance with an eleventh aspect of the present invention, in the defect inspecting method of one of the eighth to tenth aspects, the comparison of the pupil images is a comparison of a luminance distribution in a radial direction of the obtained pupil image to a luminance distribution in a radial direction of the previously-stored pupil image.

In accordance with a twelfth aspect of the present invention, in the defect inspecting method of one of the eighth to eleventh aspects, the detection of the defect is performed based on a threshold and a difference between a luminance distribution of the obtained pupil image and a luminance distribution of the previously-stored pupil image.

In accordance with a thirteenth aspect of the present invention, a defect inspecting method for inspecting a defect in a sample, a pattern being formed in a sample surface, is proposed. The defect inspecting method includes epiilluminating the sample surface with light emitted from the light source and transmitted through a polarizer and an objective lens; obtaining a pupil image of the objective lens with the light of illumination reflected from the sample surface and transmitted through the objective lens and an analyzer, the analyzer satisfying a cross-nichols condition along with the polarizer; and comparing portions to each other to detect the defect in the sample, the portions being symmetrical in relation to an optical axis of the pupil image.

In accordance with a fourteenth aspect of the present invention, in the defect inspecting method of one of the eighth to thirteenth aspects, instead of the cross-nichols relationship between the polarizer and the analyzer, an angle formed between a transmission axis of the polarizer and a transmission axis of the analyzer is set within a range of 65° to 89° by rotating one of the polarizer and the analyzer about an optical axis thereof.

In accordance with a fifteenth aspect of the present invention, in the defect inspecting method of one of the eighth to fourteenth aspects, a high-sensitive point is adopted in the pupil image when detecting the defect in the sample.

Accordingly, the present invention can provide the surface inspecting apparatus and the surface inspecting method which can make the distinction between the acceptable and defective pattern shapes on the inspected substrate in a short time irrespective of whether the inspected substrate has a resist pattern or a post-etching pattern.

BEST MODE FOR CARRYING OUT THE INVENTION

Figure 1:
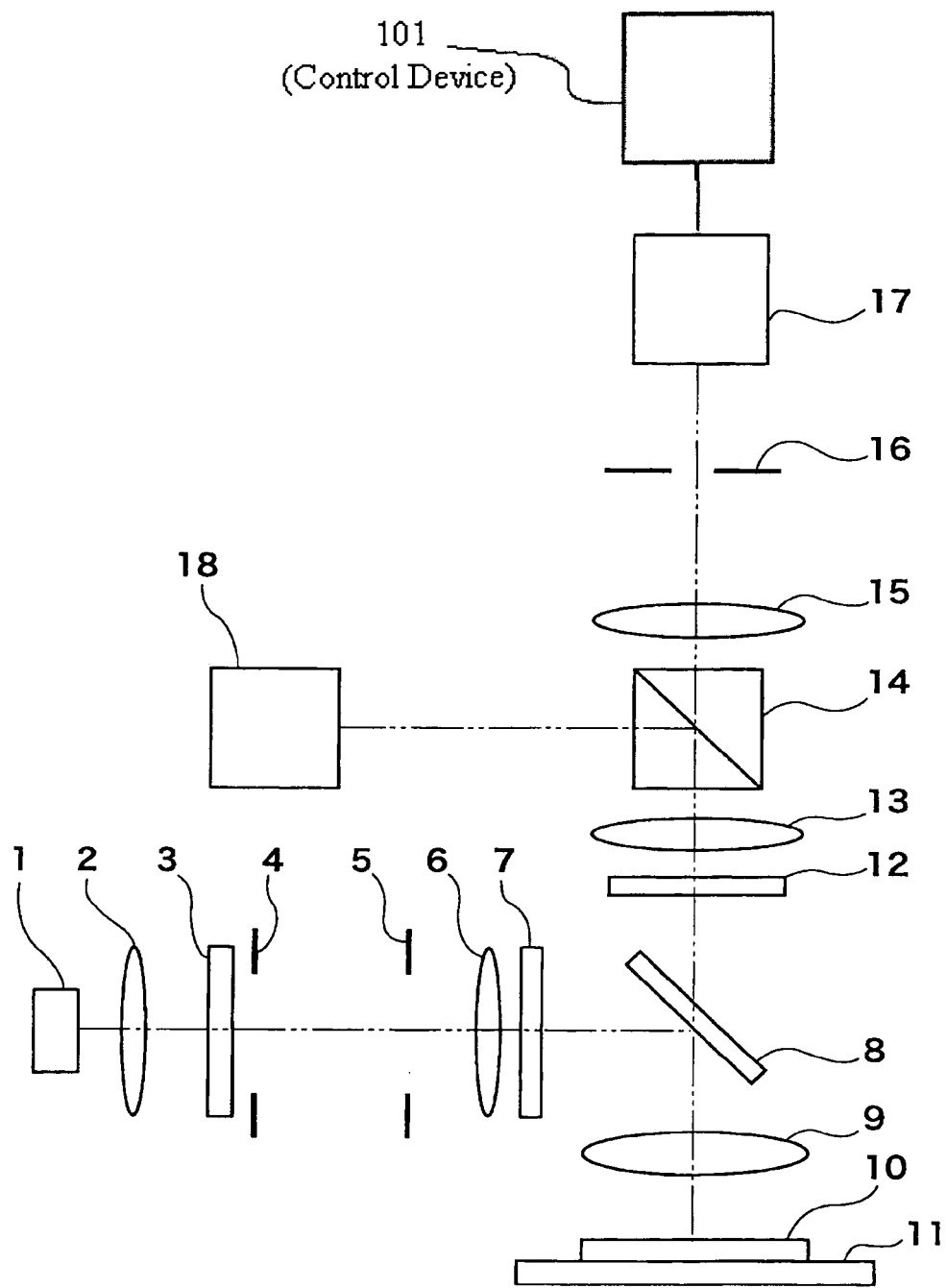
FIG. 1 is a view showing an outline of a defect inspecting apparatus according to an example of an embodiment of the present invention.

Examples of the embodiment of the present invention will be described below with reference to the drawings. FIG. 1 is a view showing an outline of a defect inspecting apparatus according to an example of the embodiment of the present invention. The light emitted from a light source 1 (such as a white-light LED and a halogen lamp) travels through a lens 2, an illuminance homogenizing unit 3 including an interference filter, an aperture stop 4, and a field stop 5 and is collimated by a lens 6. The aperture stop 4 and the field stop 5 have structures in which an aperture shape and an aperture position are changeable with respect to an optical axis. Therefore, an angular aperture of the illumination can be changed while a size and a position of an illumination region can be changed.

The collimated light having traveled through a detachable polarizer 7 is reflected by a half mirror 8 and guided to an objective lens 9 for coaxial epi-illumination of a wafer 10 placed on a wafer stage 11. The wafer stage 11 can be moved in orthogonal three directions, that is, x-axis, y-axis, and z-axis directions, and the wafer stage 11 can be θ-rotated about the z-axis is illuminated with the coaxially incident light. (The optical axis of the coaxial epi-illumination is set at the z-axis).

The light for the coaxial epi-illumination of the wafer 10 is reflected by the wafer 10 and returned to the objective lens 9. The light is transmitted through the half mirror 8, travels through a detachable analyzer 12 and a lens 13 and is incident to a half prism 14. The light reflected by the half prism 14 forms an image of the wafer 10 on an imaging device 18. The light transmitted through the half prism 14 is further transmitted through a lens 15. Then the light forms an image of the wafer 10 on a field stop 16, and forms a pupil image of the objective lens 9 on an imaging device 17. The field stop 16 can be moved in the x-axis and y-axis directions with respect to the optical axis (z-axis), and the field stop 16 has an aperture shape variable function.

A pupil image (reference image) of a sound pattern, previously taken by the imaging device 17, is stored in a control device 101. The pupil image (reference image) is compared to a pupil image (detected image) which is of the inspection object, and a defect is detected by detecting a difference between the pupil images.

Alternatively, for example, luminance of the reference image and luminance of the detected image are compared to each other in each pixel, and the determination that a defect exists may be made when the difference of luminance exceeds a predetermined threshold in a certain pixel. It is not necessary that the comparison is not performed for all the pixels, but the comparison is performed only for the pixels on a predetermined line (radial direction) passing through the optical axis as described later.

When a defect exists, symmetry of the reflected light is lost to generate a difference in luminance or hue between portions which are symmetrical in relation to the optical axis of the pupil image. Therefore, a defect can be detected by detecting the difference.

Figure 2:
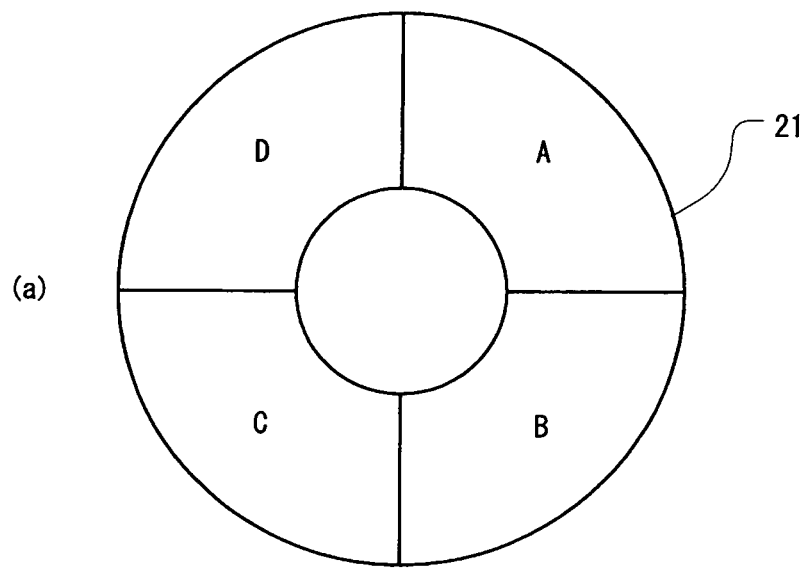
FIG. 2 is a view showing examples of a pupil image divided for observation.
Figure 2:
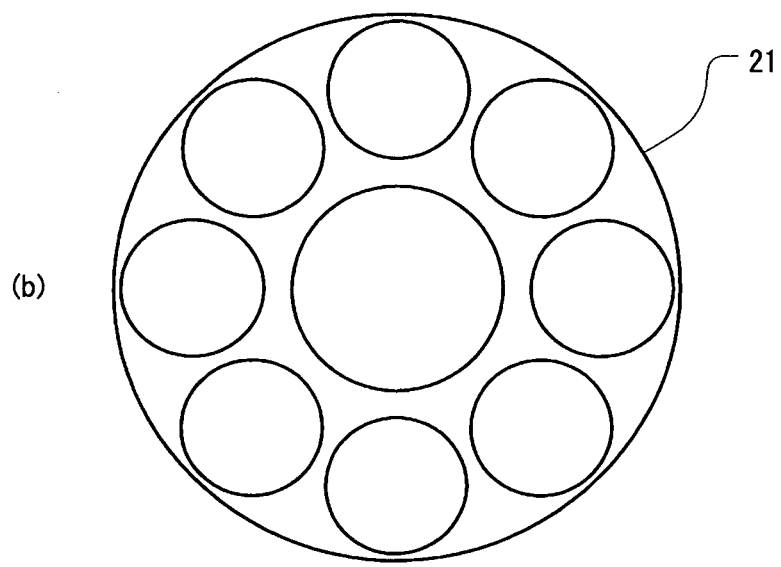

Alternatively, the pupil image is divided into an inside and an outside of a circle corresponding to the angle of 45° of the light incident to wafer, and a difference between the reference image and the detected image is detected in the inside and outside of the circle, and a defect may be detected based on the result of the difference. Additionally, as shown in FIG. 2(a), a pupil image 21 is divided into A, B, C, D, and D portions, a difference between the reference image and the detected image is detected in each portion, and a defect may be detected based on the result of the difference. As shown in FIG. 2(b), a difference between the reference image and the detected image is detected in nine portions shown by circles in the pupil image 21, and a defect may be detected based on the result of the difference. In the drawings from FIG. 2, a component shown in a preceding drawing is designated by the same numeral, and sometimes description is omitted.

The reason why the comparison of pupil images (images on a pupil plane of the objective lens) is used as the defect detecting method is that, in the image of the simple wafer surface, a pattern pitch becomes not more than resolution of the inspecting apparatus and a defect cannot optically be detected.

The aperture position and the aperture shape can be changed in the field stop 16. Therefore information on a region having a desired size can be detected at a desired position of the wafer 10. Because the polarizer 7 and the analyzer 12 are set so as to satisfy a cross-nichols condition, an observed light quantity substantially becomes zero as long as a polarization principal axis is not rotated by the pattern of the wafer 10, except for the case where there exist an influence of the rotation of the polarization principal axis of the objective lens as described later.

In the embodiment, illumination σ (NA of illumination light source/NA of objective lens) is variable by the aperture stop 4, so that the wafer 10 can be illuminated with proper brightness.

Figure 3:
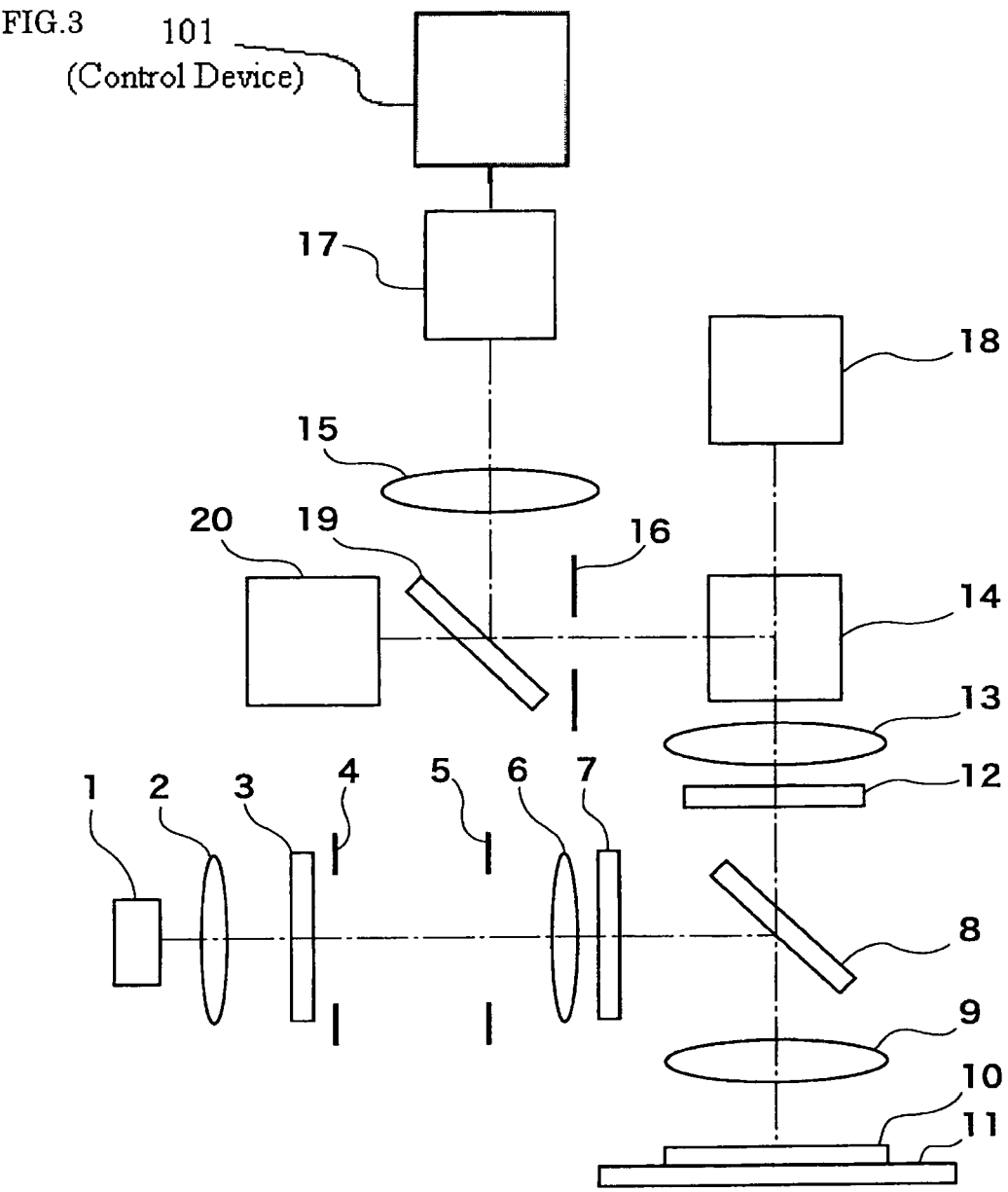
FIG. 3 is a view showing an outline of a defect inspecting apparatus according to another example of the embodiment of the present invention.

FIG. 3 is a view showing an outline of a defect inspecting apparatus according to another example of the embodiment of the present invention. The defect inspecting apparatus of FIG. 3 differs from the defect inspecting apparatus of FIG. 1 in that the light transmitted through the half prism 14 reaches the imaging device 18, in that a half mirror 19 and a light source 20 are provided and the light reflected by the half prism 14 is reflected by the half mirror 19 to reach the imaging device 17, and in that a position of the field stop 16 and that of the lens 15 is replaced with each other. Additionally, the defect inspecting apparatus of FIG. 3 differs from the defect inspecting apparatus of FIG. 1 in that aperture stops having plural different shapes are provided and one aperture stop 4 is selected and inserted into the optical path as described later. Because the defect inspecting apparatus of FIG. 3 is identical to the defect inspecting apparatus of FIG. 1 in other points, only the portions different from each other will be described while the description is omitted for the same portions.

Figure 4:
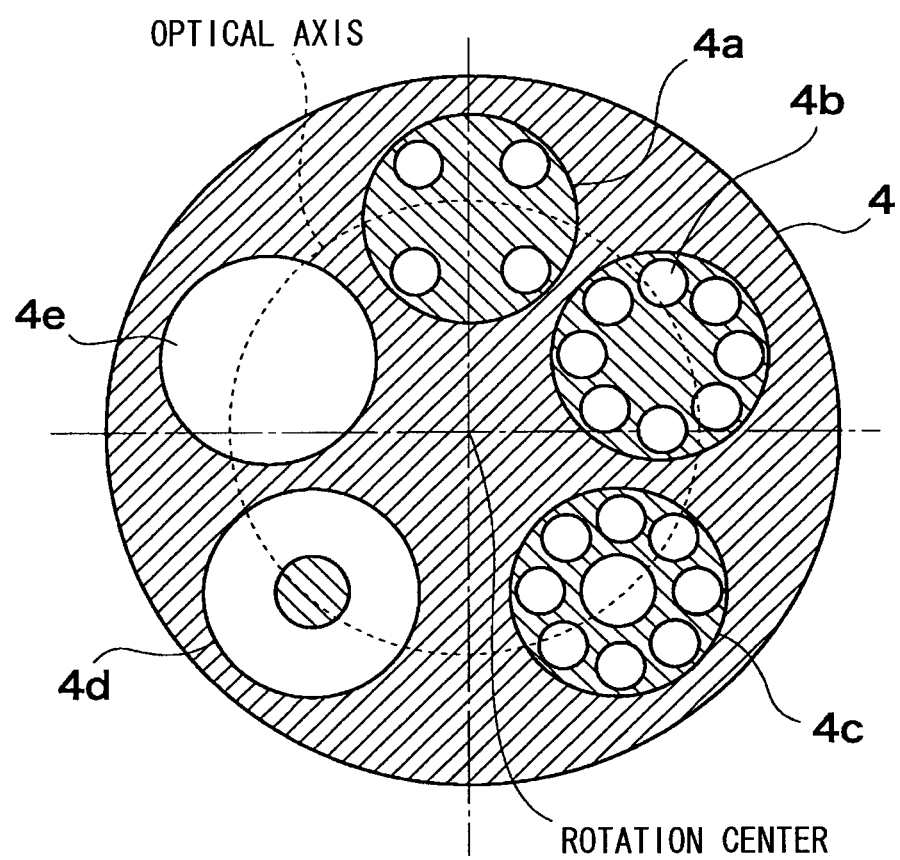
FIG. 4 is a view showing an example of an aperture stop including plural unit aperture stops.

For example, the aperture stop 4 includes unit aperture stops 4a, 4b, 4c, 4d, and 4e shown in FIG. 4, and one of the unit aperture stops 4a, 4b, 4c, 4d, and 4e can be selected for use by rotating the aperture stop 4.

The unit aperture stop 4a includes four apertures as shown in FIG. 4, the unit aperture stop 4b includes eight apertures as shown in FIG. 4, the unit aperture stop 4c includes nine apertures as shown in FIG. 4, the unit aperture stop 4d includes an aperture in which light shielding is performed in a central portion as shown in FIG. 4, and the unit aperture stop 4e includes only an aperture as shown in FIG. 4. A diameter of each aperture may be variable. A light source (such as a white-light LED and a halogen lamp) may be disposed at each aperture.

An incident angle of the illumination light is selected depending on a type of the wafer 10. When the wafer 10 is illuminated only with the illumination light having a particular incident angle, defect detecting performance is sometimes enhanced. Therefore, the inspection is performed while the incident angle of the illumination light is changed by sequentially selecting the unit aperture stops 4a, 4b, 4c, 4d, and 4e, and the inspection result having the best detecting performance may be adopted. In the case where the optimum unit aperture stop corresponding to the type of the wafer has been found by previously-performed inspection, the inspection can be performed with the optimum unit aperture stop from the beginning.

When the wafer 10 is excessively illuminated with the illumination light, disadvantageously damage is caused to the wafer depending on the type of wafer 10. In such cases, the light quantity of the illumination light can be decreased by selecting the unit aperture stops 4a, 4b, 4c, and 4d, thereby eliminating the damage to the wafer 10.

In performing the inspection, sometimes a wide range is taken in the image of the wafer 10 observed by the imaging device 18 while the pupil image of the wafer 10 observed by the imaging device 17 is restricted to a particular narrow range of the wafer 10. In such cases, the aperture of the field stop 5 is increased to illuminate the wide range of the wafer 10, the aperture of the field stop 16 is decreased to a particular aperture position, and a visual field is narrowed to a particular range.

At this point, it is not found which range of the wafer 10 corresponds to the pupil image to be observed by the imaging device 17. Therefore, the embodiment includes the light source 20. The illumination light emitted from the light source 20 is transmitted through the half mirror 19 and the field stop 16 and reflected by the half mirror 14, and the light forms the image of the field stop 16 on the surface of the wafer 10 through the epi-illumination optical system including the lens 13, analyzer 12, half mirror 8, and objective lens 9. It is found which range of the wafer 10 corresponds to the pupil image to be observed with the imaging device 17 by observing the image with the imaging device 18. In the case where the light emitted from the light source 20 obstructs the inspection, for example, the light source 1 may be used by switching the light source 20 to the light source 1. The light source 20 is lit on only when a region of the wafer 10 which corresponds to the pupil image to be observed with the imaging device 17 is determined, and the light source 20 may be turned off in the actual inspection.

EXAMPLES

Figure 5:
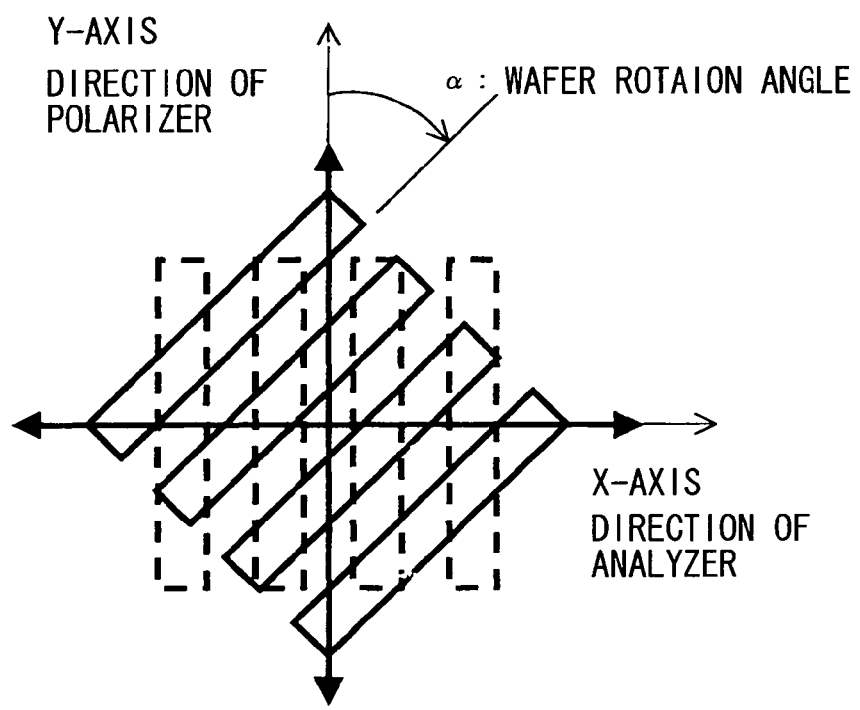
FIG. 5 is a view showing positional relationships between directions of an analyzer and a polarizer and a wafer including an L/S pattern.

FIG. 5 is a view showing positional relationships between directions of the analyzer and polarizer and the wafer including the L/S pattern. Referring to FIG. 5, a direction of the analyzer is set at an X-axis direction, a direction of the polarizer is set at a Y-axis direction, and the repetition direction of the L/S pattern is rotated by α from the Y-axis direction to the X-axis direction.

Figure 6:
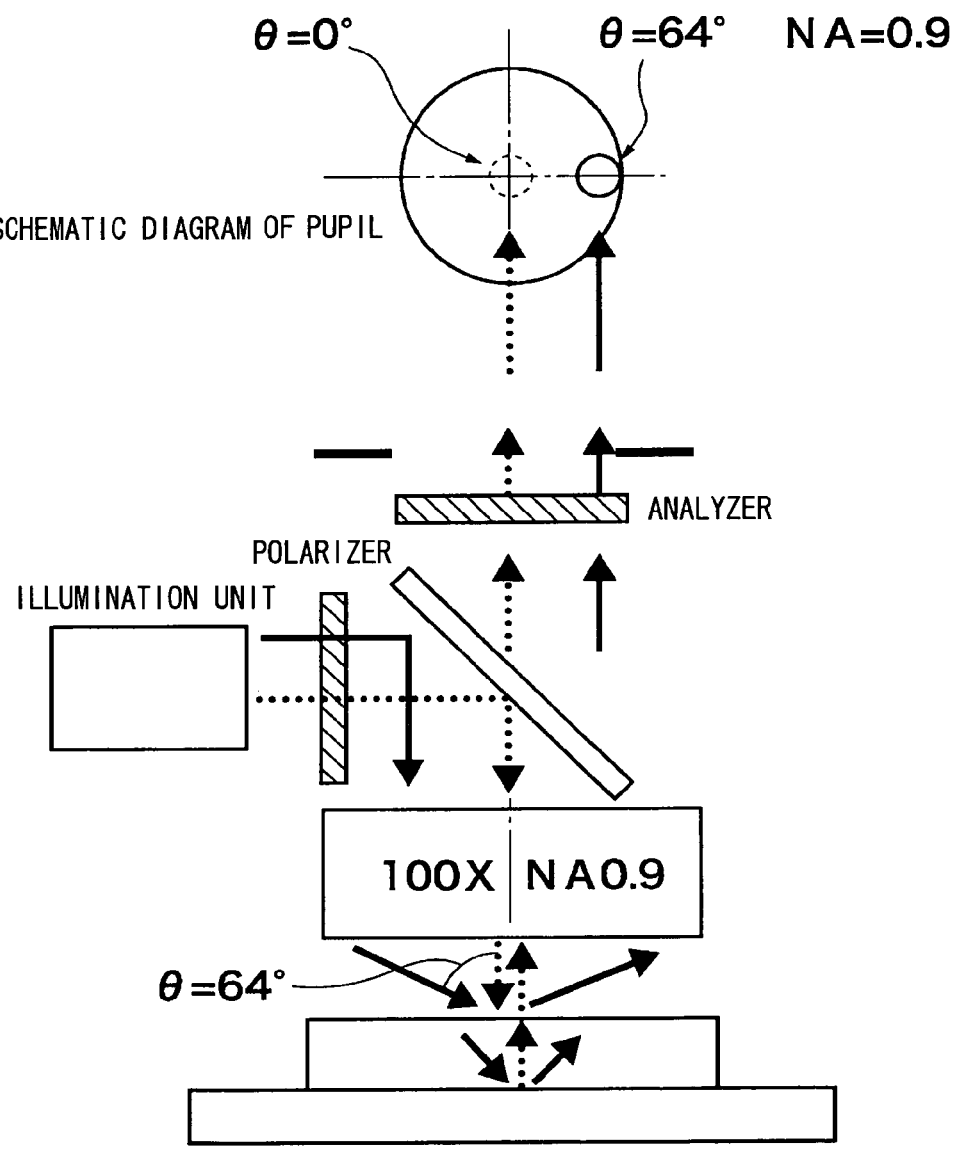
FIG. 6 is a view explaining a relationship between an incident angle of illumination light to a wafer and a position in a pupil.

A relationship between the angle of the illumination light incident to the wafer and the position in the pupil will be described with reference to FIG. 6. The angle of 0° incident to the wafer is located in a pupil center on the pupil as shown by a broken-line arrow of FIG. 6. On the other hand, the incident angle of 64° (corresponding to NA=0.9) is located in an outermost peripheral of the pupil as shown by a solid-line arrow. Accordingly, the incident angle corresponds to the position in the radial direction in the pupil. That is, lights which form images at the positions having the same radius around the optical axis in the pupil are lights incident to the wafer at the same angle.

An example in which a light quantity distribution formed in the pupil by the light, specularly reflected from the 45 nm L/S resist pattern and transmitted through the analyzer, is determined by a vector analysis technique using the objective lens having NA of 0.9 will be described below.

Figure 7:
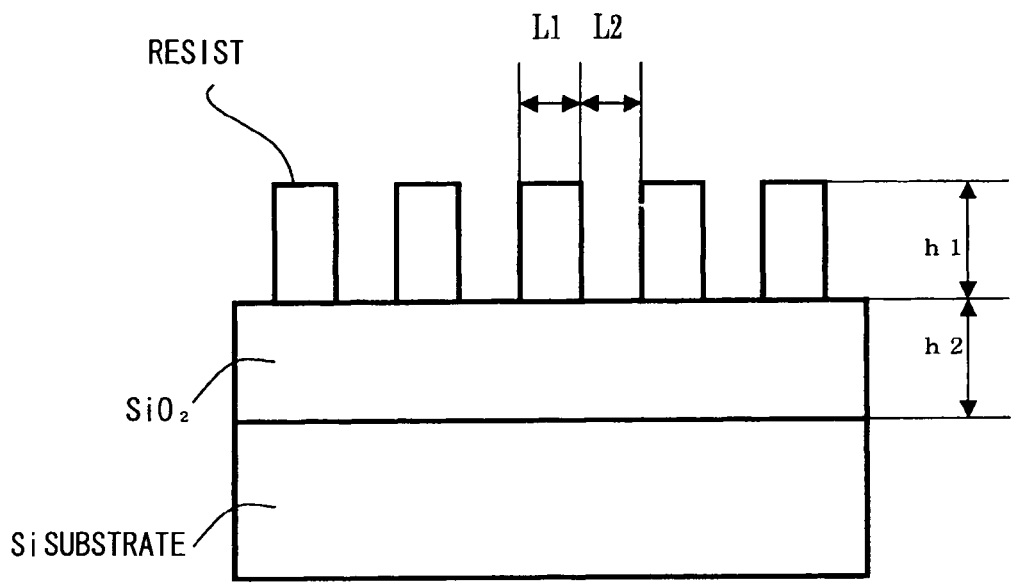
FIG. 7 is a schematic diagram showing an ideal shape of an L/S resist pattern.

FIG. 7 is a schematic diagram showing an ideal shape of the 45 nm L/S resist pattern when a vector analysis is performed. In FIG. 7, a resist width L1 and a space width L2 are set to 45 nm, a resist thickness h1 is set to 110 nm, and a $SiO_2$ thickness h2 is set to 100 nm.

Figure 8:
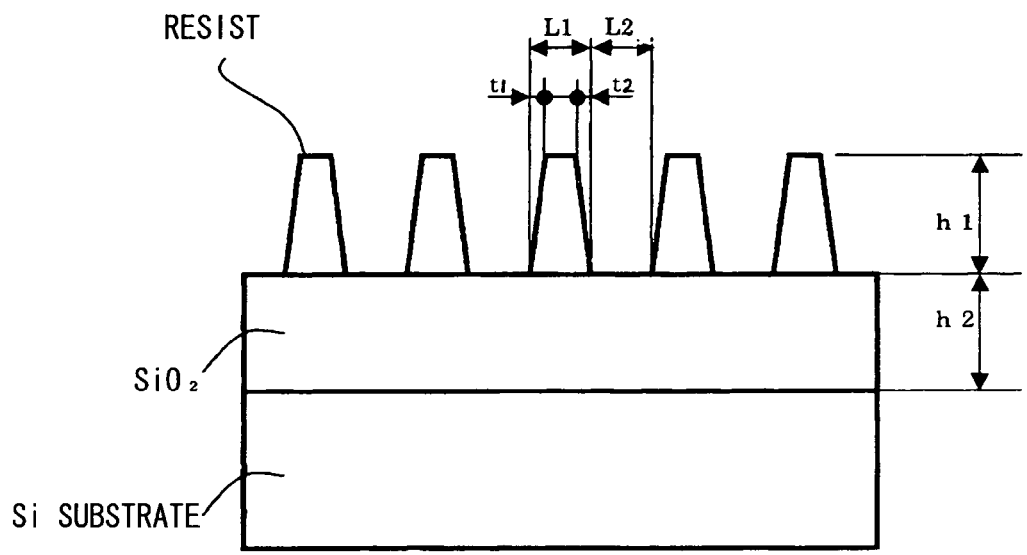
FIG. 8 is a schematic diagram showing a trapezoidal shape of the L/S resist pattern.

FIG. 8 is a schematic diagram showing a trapezoidal shape of the 45 nm L/S resist pattern. For example, in an exposure apparatus, it can be assumed that exposure is performed out of best focus to generate a trapezoidal shape change in the resist pattern. The trapezoidal shape change is expressed numerically by (t1+t2)/L1 (t1 and t2 are widths of oblique sides of the trapezoid). In the case of an ideal state, that is, a rectangular shape, the shape change becomes 0%. In the case of triangular shape, the shape change becomes 100%.

The rotation angle α of the wafer pattern of FIG. 5 is set to 45°, and the light quantity distribution formed in the pupil by the light which is specularly reflected from the 45 nm L/S resist pattern and transmitted through the analyzer is determined at the wavelength λ of 546 nm. The results are obtained as shown in FIGS. 9A to 9C.

Figure 9A:
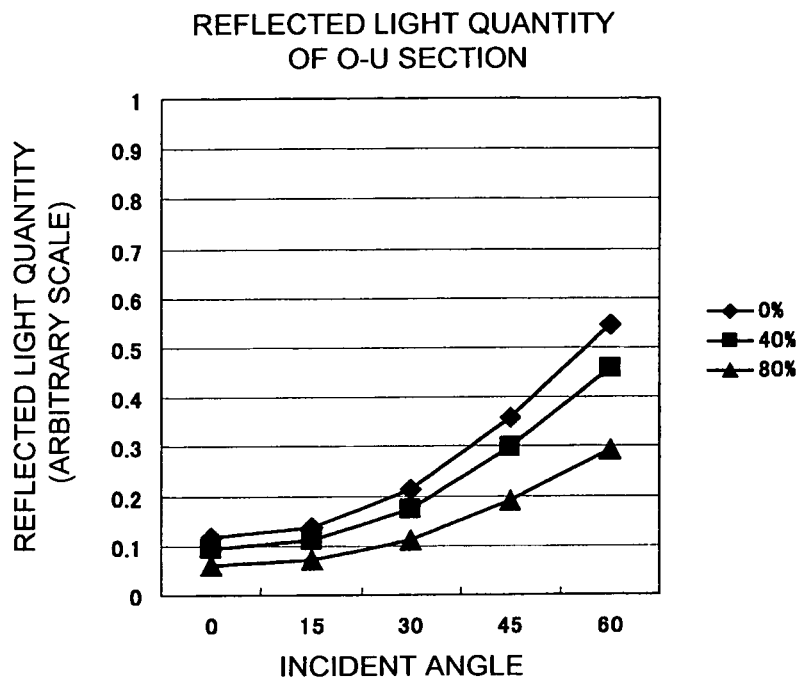
FIG. 9A is a view showing a light quantity distribution formed in the pupil by light which is specularly reflected from the L/S resist pattern and transmitted through an analyzer.
Figure 9B:
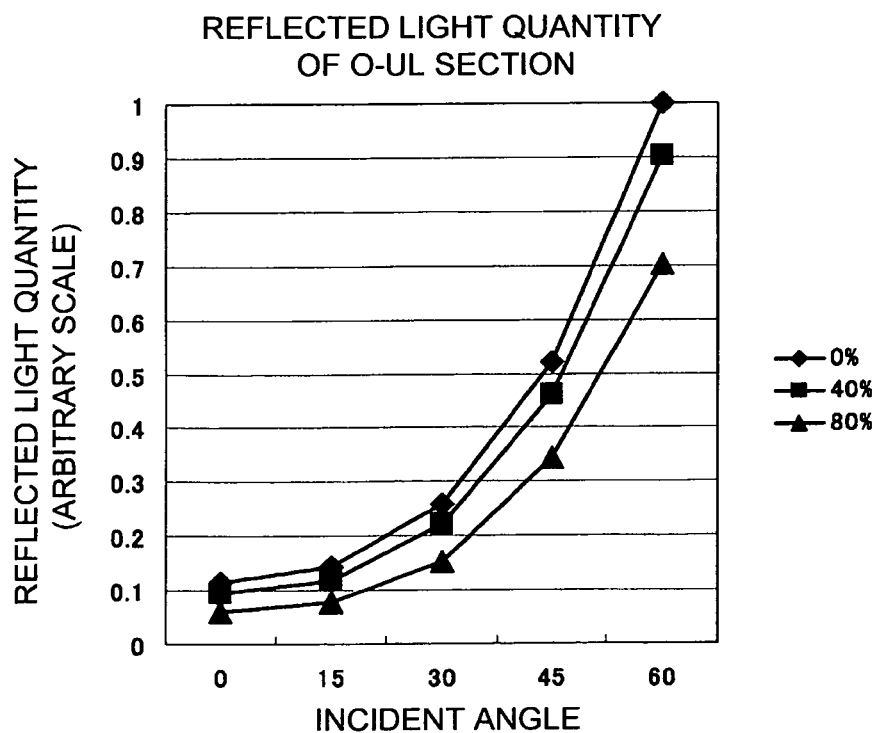
FIG. 9B is a view showing a light quantity distribution formed in the pupil by the light which is specularly reflected from the L/S resist pattern and transmitted through the analyzer.
Figure 9C:
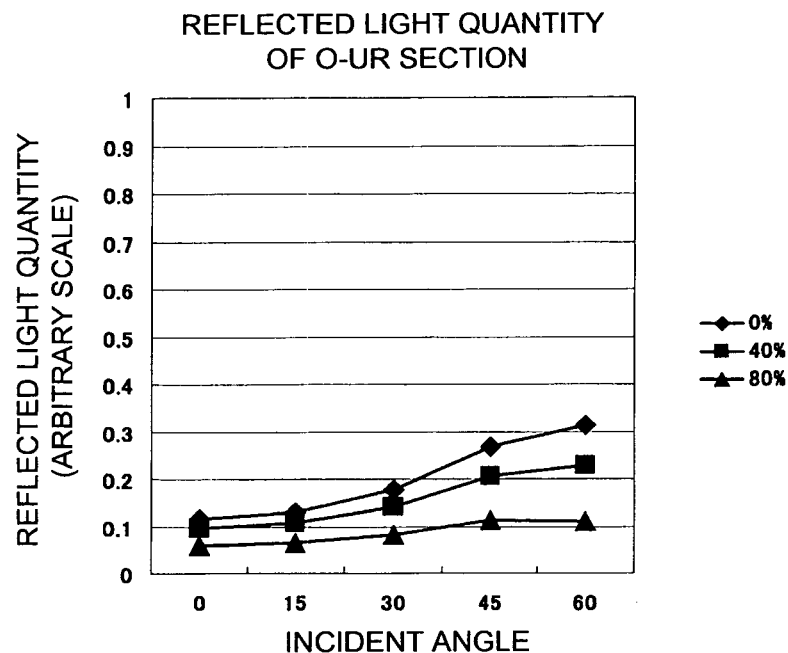
FIG. 9C is a view showing a light quantity distribution formed in the pupil by the light which is regularly reflected from the L/S resist pattern and transmitted through the analyzer.
Figure 10:
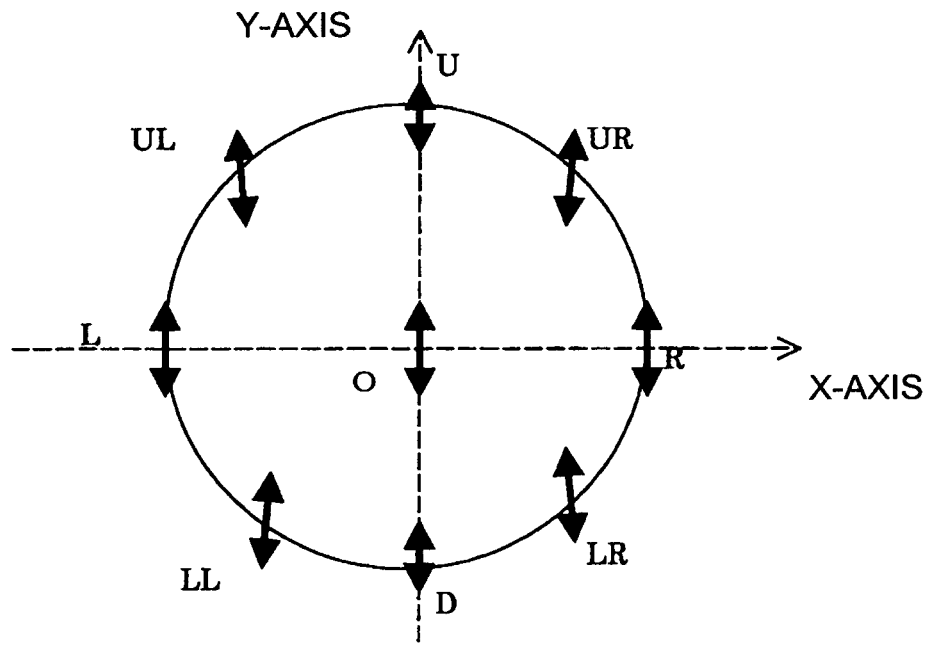
FIG. 10 is a view showing a polarization optical axis direction of reflected light at each position of the pupil.

FIGS. 9A to 9C are line graphs showing a relationship between the incident angle and the specularly-reflected light quantity in observing the L/S patterns whose shape changes become 0%, 40%, and 80%. The incident angle is set at the horizontal axis while the specularly-reflected light quantity is set at the vertical axis. FIG. 9A shows reflected light quantity in an O-U section in a pupil shown in FIG. 10, FIG. 9B shows reflected light quantity in an O-UL section in the pupil shown in FIG. 10, and FIG. 9C shows reflected light quantity in an O-UR section in the pupil shown in FIG. 10. A scale of each vertical axis of the graphs shown in FIGS. 9A to 9C is normalized such that the maximum value of the specularly-reflected light of the O-UL section is set at 1 in the shape change of 0%. Because the incident angle corresponds to the radius in the pupil as described above, the pieces of data shown in FIGS. 9A to 9C correspond to the specular reflection distribution in which the radius of each section is set at the horizontal axis.

FIG. 10 shows a polarization principal axis direction of the reflected light at each position of the pupil by arrows. The polarization axis is not rotated, but orientated toward the Y-axis direction (direction of the polarizer) in the X-axis direction and Y-axis direction (R, L, U, D, and O). However, the polarization axis is rotated by about 4.5° in the peripheral portion in the pupil in the direction (UR, LR, LL, and UL) which is inclined by 45° with respect to the X-axis and Y-axis.

As can be seen from FIGS. 9A to 9C, the reflected light quantity is increased as the incident angle is enlarged, and the reflected light quantity is lowered when the shape change is increased. Therefore, the extent of the shape change, that is, a degree of defect can be detected by comparing the reflected light quantity of the wafer having the normal L/S pattern and the reflected light quantity of the wafer which is of the inspection object.

As can be seen from FIG. 9, the reflected light quantity depends on the position in the pupil, and the O-UL section has the largest reflected light quantity. Additionally, it is also found that, at the incident angle of 60°, the O-UL section has the largest change in reflected light quantity associated with the shape change. Therefore, in the method for detecting the shape change of the 45 nm L/S pattern having the structure of FIGS. 7 and 8 in the pupil with the polarizer and the analyzer provided in the cross-nichols state, a high-sensitivity pattern defect inspection can be performed by measuring the change in light quantity near the incident angle of 60° of the O-UL section at the wavelength λ of 546 nm.

Figure 11A:
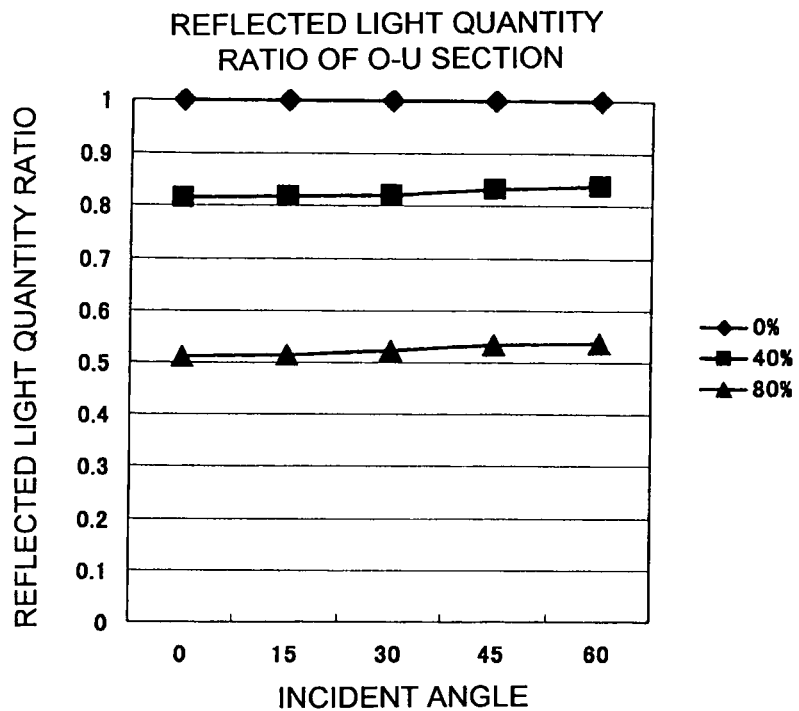
FIG. 11A is a view showing a relationship between an angle of light incident to the wafer and light quantity of specular reflection.
Figure 11B:
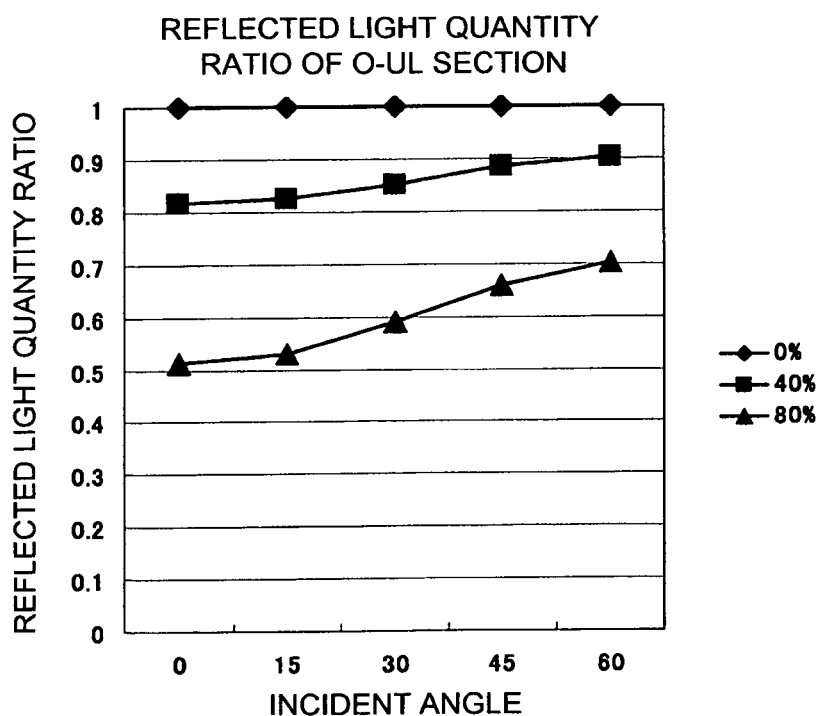
FIG. 11B is a view showing a relationship between the angle of the light incident to the wafer and the light quantity of the specular reflection.
Figure 11C:
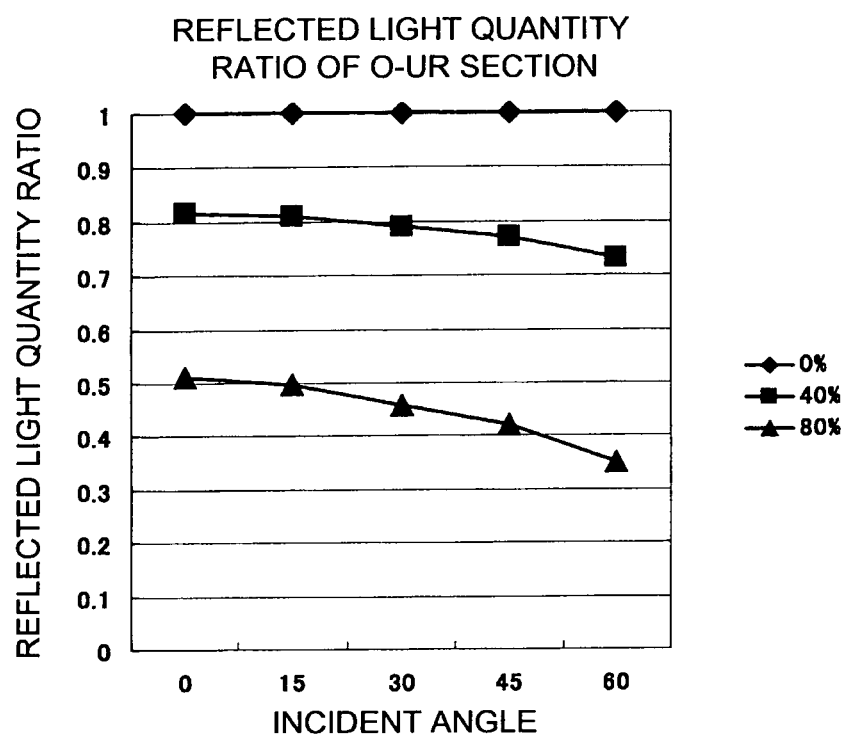
FIG. 11C is a view showing a relationship between the angle of the light incident to the wafer and the light quantity of the specular reflection.

FIGS. 11A to 11C are line graphs showing a relationship between the angle of the light incident to the wafer and a specularly-reflected light quantity ratio in observing the L/S patterns whose shape changes become 0%, 40%, and 80%. The incident angle is set at the horizontal axis while the specularly-reflected light quantity ratio is set at the vertical axis. FIG. 11A shows reflected light quantity ratio in the O-U section in the pupil shown in FIG. 10, FIG. 11B shows reflected light quantity ratio in the O-UL section in the pupil shown in FIG. 10, and FIG. 11C shows reflected light quantity ratio in the O-UR section in the pupil shown in FIG. 10. A scale of the vertical axis of FIG. 11 is normalized by the specularly-reflected light quantity at the shape change of 0%.

As can be seen from FIGS. 11A to 11C, the reflected light quantity ratio associated with the shape change depends on the incident angle and the position in the pupil. It is found that a change in specularly-reflected light quantity ratio associated with the shape change is decreased as the incident angle is enlarged in the O-UL section while a change in specularly-reflected light quantity ratio associated with the shape change is increased as the incident angle is enlarged in the O-UR section.

Therefore, in the method for detecting the shape change of the 45 nm L/S pattern having the structure of FIGS. 7 and 8 in the pupil with the polarizer and the analyzer provided in the cross-nichols state, a high-sensitivity pattern defect inspection can be performed by measuring a ratio of a change in light quantity near the incident angle of 60° of the O-UR section at the wavelength λ of 546 nm.

Accordingly, based on information on the pattern structure, the light quantity distribution in the pupil is previously obtained by the vector analysis while the shape change and the incident angle are used as the parameters. Then the position where a change in light quantity with respect to the shape change is large in the pupil and the position where a ratio of a change in light quantity with respect to the shape change is large in the pupil are preferentially selected to detect a change in light quantity or a ratio of a change in light quantity. As a result, a shape defect can be inspected with higher sensitivity.

In the example, the computation is performed using the schematic diagrams of FIGS. 7 and 8. Alternatively, the light quantity distribution in the pupil with respect to line width change is obtained by changing a ratio of the resist width L1 and the space width L2. Then the position where a change in light quantity with respect to the line width change is large in the pupil and the position where a ratio of a change in light quantity with respect to the line width change is large in the pupil are preferentially selected to detect a change in light quantity or a ratio of a change in light quantity. As a result, a line width defect can be inspected with higher sensitivity.

Alternatively, light quantity distribution in the pupil with respect to the film thickness change is obtained by changing resist thickness h1 or $SiO_2$ thickness. Then the position where a change in light quantity with respect to the film thickness change is large in the pupil and the position where a ratio of a change in light quantity with respect to the film thickness change is large in the pupil are preferentially selected to detect a change in light quantity or a ratio of a change in light quantity. As a result, a film thickness defect can be inspected with higher sensitivity.

Additionally, computation is performed while the wavelength λ is changed, the optimum wavelength λ is selected to increase the sensitivity for various defects, and the position in the pupil is selected. As a result, a shape defect can be inspected with higher sensitivity.

For example, a white-light LED is used as the light source, the light quantity distribution in the pupil is taken by a color CCD, and the light quantity distribution is divided into RGB, which allows the wavelength to be selected. The optimum pupil position is previously selected by the computation based on the pattern structure. Therefore, an RGB ratio can be detected, or a pupil image of the acceptable pattern and a pupil image of the defective pattern are stored and a defect can be inspected by the comparison of the pupil images.

Assuming that the transmission axis of the linearly polarized light of the polarizer is set at the y-axis while the transmission axis of the analyzer is set at the x-axis, light intensity of the observed pupil image which is transmitted through the analyzer is expressed by the following equation in U, R, D, and L of the pupil of FIG. 10:

[Equation 1]

$$I = Ax^2$$

where Ax is an amplitude of a vibration component in the x-direction.

On the other hand, in the diagonal directions UR, UL, LR, and LL of the pupil of FIG. 10, the polarization principal axis of the objective lens 9 is rotated by ±4.5°. Assuming that θ is the rotation amount of ±4.5°, the light intensity of the observed pupil image which is transmitted through the analyzer is expressed by the following equation:

[Equation 2]

$$I_\theta = |\cos\theta \cdot Ax \cdot \exp(i\delta_x) + \sin\theta \cdot Ay \cdot \exp(i\delta_y)|^2$$

where Ax and Ay are amplitudes of the vibration components in the x-direction and the y-direction and $\delta_x$ and $\delta_y$ are phases of the vibration components in the x-direction and the y-direction.

Assuming that the polarization principal axis rotated clockwise is set to positive (+) while the polarization principal axis rotated counterclockwise is set to negative (−), the polarization principal axis is rotated by θ=+4.5° in UR and LL while the polarization principal axis is rotated by θ=−4.5° in UL and LR. Accordingly, the light intensity in UR, that in LL, that in UL and that in LR are different from that in U, R, D, and L. Further, the light intensity in UR and LL is different from that in UL and LR. Therefore, changes in luminance and hue are recognized in the pupil according to the pattern shape, and a defect inspection can be performed by a difference with the acceptable pattern.

Figure 12:
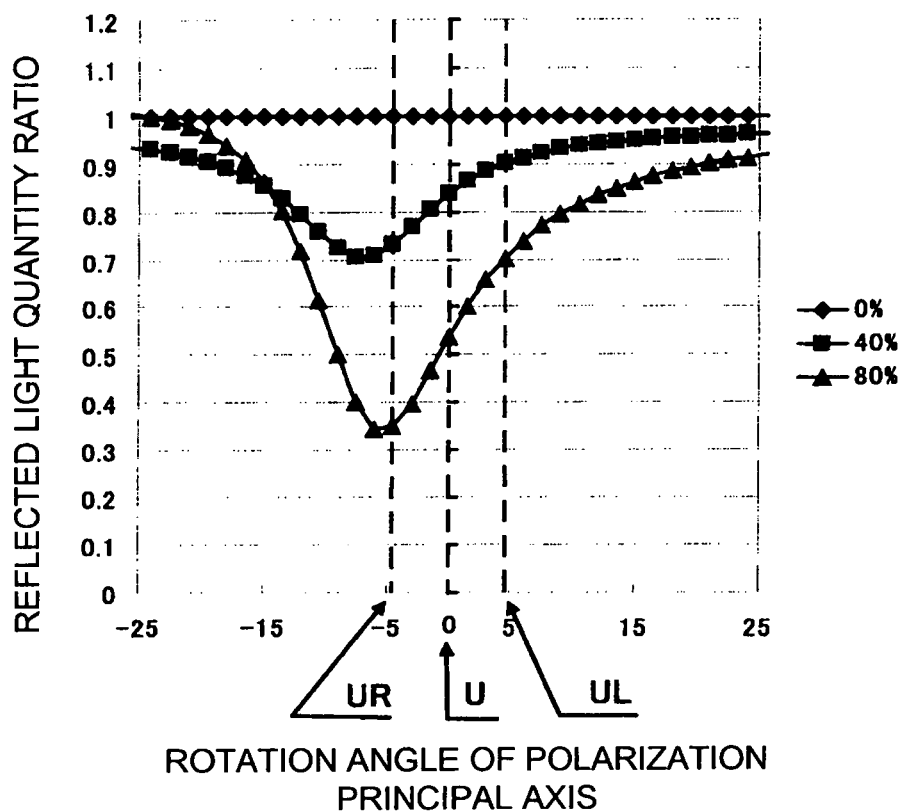
FIG. 12 is a view showing a light quantity formed in the pupil by the light which is specularly reflected from the L/S resist pattern and transmitted through the analyzer, wherein the light quantity is computed at a wavelength $\lambda$ of 546 nm and an incident angle of 60° while an L/S resist pattern azimuth angle $\alpha$ is set at 45°.
Figure 13:
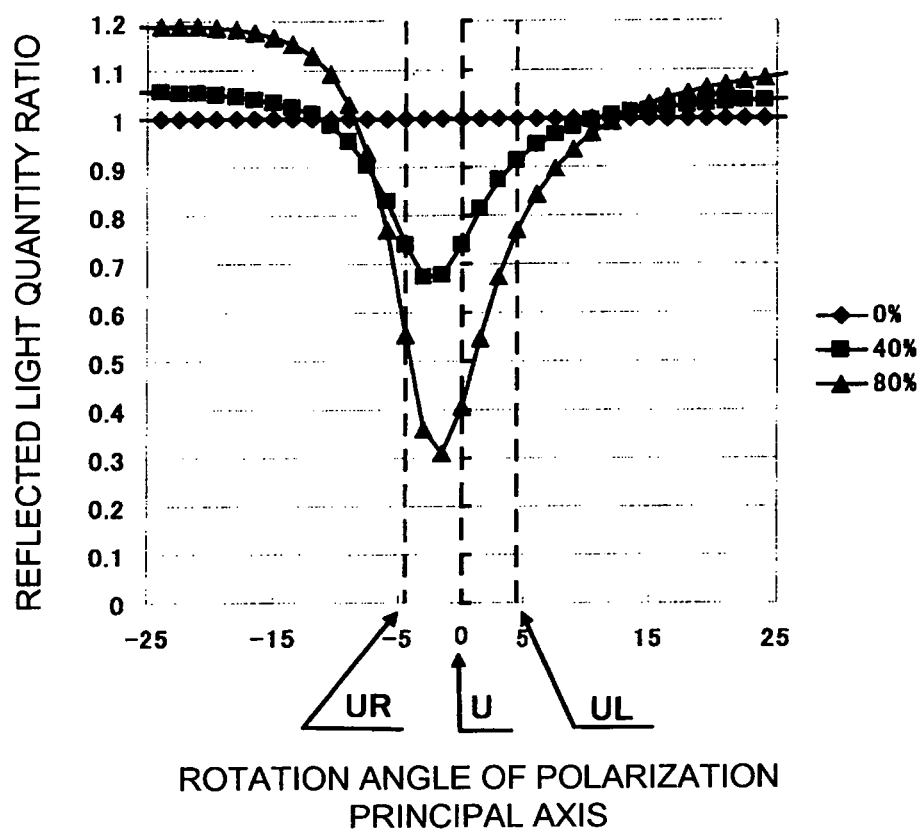
FIG. 13 is a view showing a light quantity formed in the pupil by the light which is specularly reflected from the L/S resist pattern and transmitted through the analyzer, wherein the light quantity is computed at a wavelength $\lambda$ of 436 nm and an incident angle of 60° while an L/S resist pattern azimuth angle $\alpha$ is set at 45°.

Thus, the effect of the rotation amount of θ=±4.5° of the polarization principal axis in the objective lens 9 is described. FIGS. 12 and 13 show study results for the optimum range of the rotation amount θ. In the line graph of FIG. 12, the wavelength λ is set to 546 nm, the rotation angle α in the periodic direction of the L/S pattern is set to 45°, the incident angle is restricted to 60°, the rotation angle of the polarization principal axis is set at the horizontal axis, the specularly-reflected light quantity is set at the vertical axis, and the relationship is shown when the 45 nm L/S patterns having the shape changes of 0%, 40%, and 80% are observed with a range of the rotation angle of the polarization principal axis between −25° to +25°. In FIG. 12, the reflected light quantity is normalized by the specularly-reflected light quantity at the shape change of 0%.

UL and UR shown by arrows in FIG. 12 correspond to the rotation amount of ±4.5° of the polarization principal axis of the objective lens 9 having NA of about 0.9. As can be seen from FIG. 12, a change amount of reflected light quantity ratio associated with the shape change is larger at UR than at UL and a change amount of reflected light quantity ratio associated with shape change becomes larger than that at UR when the rotation amount of the polarization principal axis becomes −7.5°.

In the line graph of FIG. 13, the wavelength λ is set to 436 nm, the rotation angle α in the periodic direction of the L/S pattern is set to 45°, the incident angle is restricted to 60°, the rotation angle of the polarization principal axis is set at the horizontal axis, the specularly-reflected light quantity is set at the vertical axis, and relationship is shown when the 45 nm L/S patterns having the shape changes of 0%, 40%, and 80% are observed with a range of the rotation angle of the polarization principal axis between −25° to +25°. In FIG. 13, the reflected light quantity is normalized by the specularly-reflected light quantity at the shape change of 0%.

UL and UR shown by arrows in FIG. 13 correspond to the rotation amount of ±4.5° of the polarization principal axis of the objective lens 9 having NA of about 0.9. As can be seen from FIG. 13, a change amount of reflected light quantity ratio associated with the shape change is larger at UR than at UL, and a change amount of reflected light quantity ratio associated with shape change becomes larger than that at UR when the rotation amount of the polarization principal axis becomes −1.5°.

Therefore, the wavelength, the incident angle, and the rotation amount of polarization principal axis are selected to measure a ratio of a change in light quantity, such that a pattern defect can be inspected with high sensitivity. It is found that the optimum rotation amount of polarization principal axis ranges from 1° to 25°.

In order to change the rotation amount of polarization principal axis, plural objective lenses having different phase characteristics of anti-reflection coatings deposited on the lens surface thereof are prepared, and one of the objective lenses can be selected for use. The rotation amount of polarization principal axis can be changed by losing the cross-nichols relationship between the polarizer and the analyzer. A mechanism which can be rotated about the optical axis is provided in the polarizer or the analyzer, and desirably the polarizer or the analyzer is rotated about the optical axis such that an angle formed between the transmission axis of the polarizer and the transmission axis of the analyzer becomes in the range of 65° to 89° (as a result, the rotation amount of polarization principal axis can be set within the range of 1° to 25°).

The method for recognizing changes in luminance and hue in the pupil can be realized with a white-light LED which is of the light source and a color CCD imaging device. Because the changes in luminance and hue become large in a particular position in the pupil, the pupil may be divided, such that changes in luminance and hue in divided areas in the pupil are measured by spectral measurement to compare the result with that of the acceptable pattern for defect inspection. In order to recognize an asymmetry of the pattern shape, symmetric positions in the pupil are effectively selected in relation to the optical axis to measure changes in luminance and hue. Desirably the pupil is divided into the inside circle and the outside circle based on the angle of 45 degrees of the light incident to the wafer, and the changes in luminance and hue are measured.

In the examples mentioned above, the measurement is performed while the rotation angle α of the wafer pattern is set to 45°. In the case where the rotation angle α is set to 0° or 90°, even if a defect of the wafer pattern exists, the rotation of the polarization axis does not appear too much, and the defect detecting performance is lowered. Therefore, it is believed that the rotation of the polarization axis caused by the defect of the wafer pattern is increased to improve the defect detecting performance when the rotation angle α is set to 45° which is middle between 0° and 90°.

Figure 14:
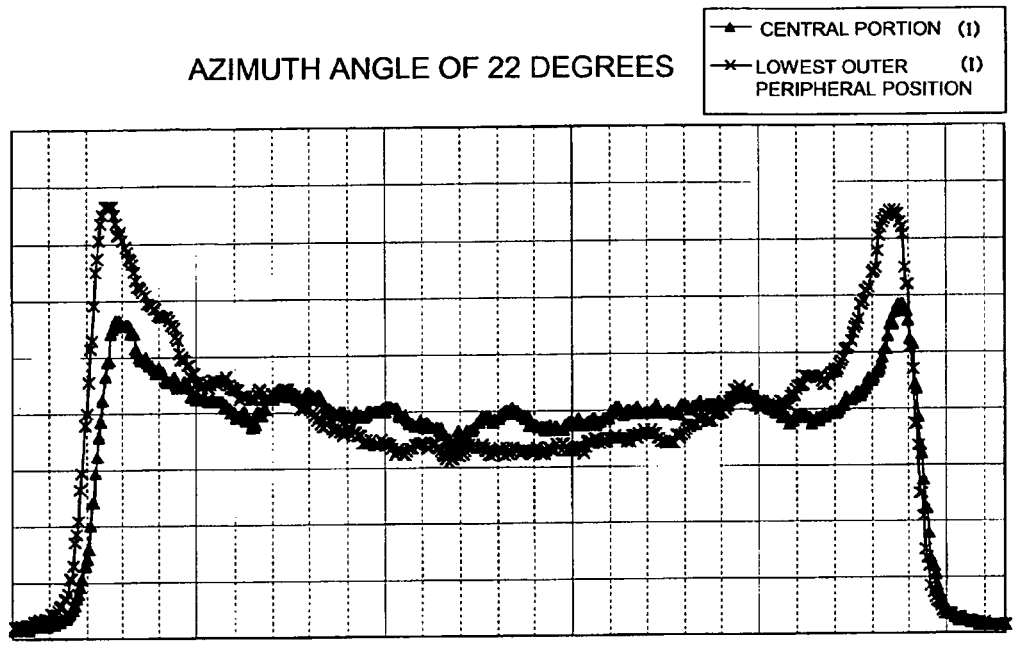
FIG. 14 is a view showing a reflected light quantity distribution in a pupil radial direction when measurement is performed at different points of the wafer while a wafer pattern rotation angle $\alpha$ is set at 22.5°.
Figure 15:
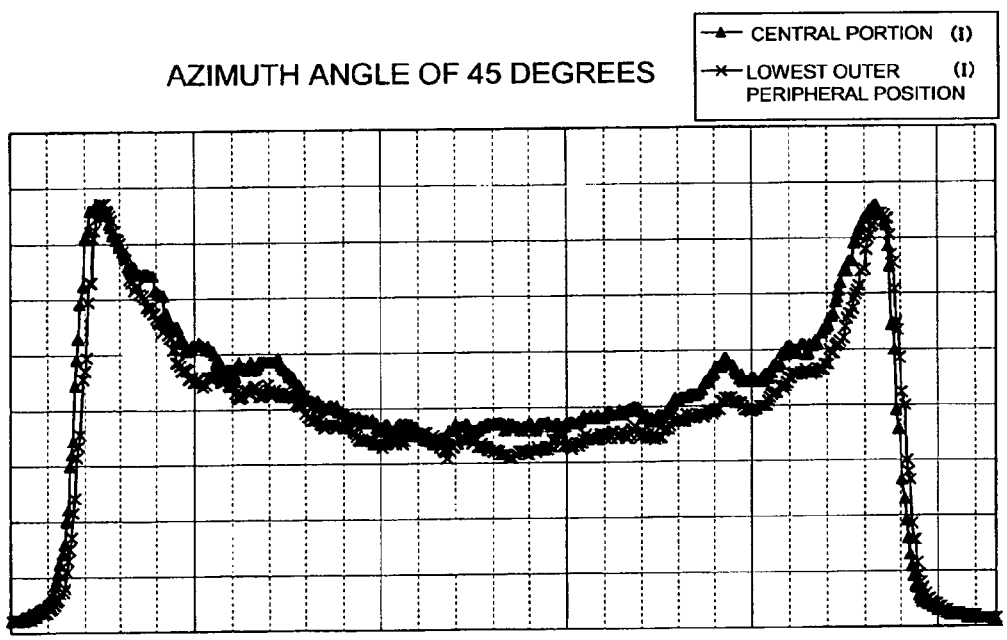
FIG. 15 is a view showing a reflected light quantity distribution in a pupil radial direction when measurement is performed at different points of the wafer while a wafer pattern rotation angle $\alpha$ is set at 45°.
Figure 16:
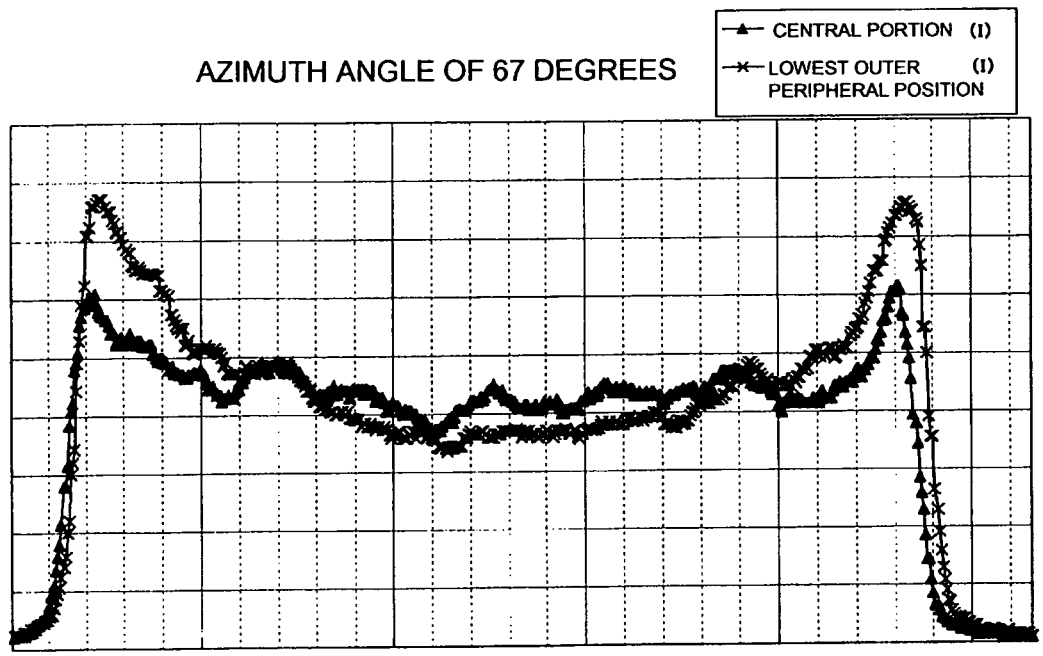
FIG. 16 is a view showing a reflected light quantity distribution in a pupil radial direction when measurement is performed at different points of the wafer while a wafer pattern rotation angle $\alpha$ is set at 67.5°.

FIGS. 14 to 16 show results in which two points (central portion and lowermost outer peripheral portion) within a particular exposure range in the wafer are measured while the rotation angle α is changed to 22.5°, 45°, and 67.5°. FIG. 14 shows the result at the rotation angle α of 22.5°, FIG. 15 shows the result at the rotation angle α of 45°, and FIG. 16 shows the result at the rotation angle α of 67.50. Each result shows the reflected light quantity distribution in the section of the UL-LR direction of FIG. 10. The horizontal axis indicates position (angle of the light incident to the wafer) in the radial direction in the pupil and the vertical axis indicates reflected light quantity. The central portion and the lowermost outer peripheral portion within the exposure range (rectangular region) of the projection lens of the exposure apparatus are adopted as the two points within the particular exposure range in the wafer.

As can be seen from the FIGS. 14 to 16, a difference in light quantity distribution is not clearly observed between the two points within the exposure range at the rotation angle α of 45°, while a large difference appears in the peripheral portion (portion having the large angle of the light incident to the wafer) in the pupil at the rotation angle α of 22.5° and 67.5°. Because the differences are attributed to minute difference of the L/S pattern in each portion of the wafer, it is found that probably a defect which cannot be detected at the rotation angle α of 45° can be detected by setting the rotation angle α of 22.5° or 67.5°.

In the light reflected from the pattern having structural birefringence, the phase difference, the amplitude Ax and the amplitude Ay are changed between the component (Y-axis direction component) parallel to the vibration plane of the incident light and the component (X-axis direction component) perpendicular to the vibration plane according to the thickness h and the shape of the wafer. Therefore, the light reflected from the pattern having structural birefringence becomes elliptically polarized light. The phase difference, the amplitude Ax and the amplitude Ay are also changed between the component parallel to the vibration plane of the incident light and the component perpendicular to the vibration plane according to the angle of the light incident to the wafer surface and the wavelength.

Figure 17:
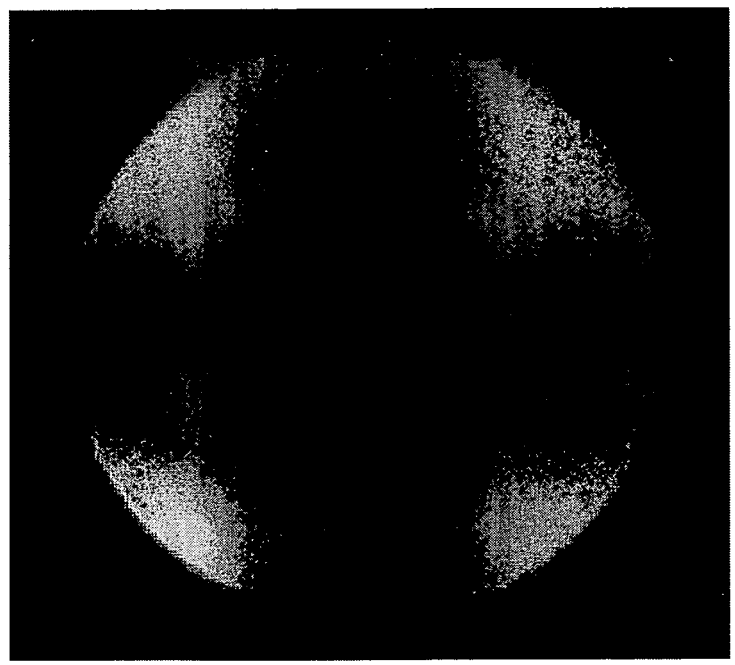
FIG. 17 is a view showing an observation image which is obtained when a bare wafer is observed with the apparatus of FIG. 1.

The bare wafer is set on the stage, and the transmission axis of the polarizer is vertically set in the pupil while the transmission axis of the analyzer is horizontally set in the pupil using the objective lens 9 having NA of about 0.9 such that the polarizer and the analyzer are orthogonal to each other to establish the cross-nichols condition. Then the pupil image observed by the imaging device 17 becomes four-leaf shape whose central portion is dark as shown in FIG. 17.

This is a phenomenon in which angle of the light incident to the objective lens surface is increased as NA of the objective lens 9 is increased and the polarization principal axis is rotated. In the example, in the objective lens having NA of 0.9, the polarization principal axis is rotated up to about 4.5 degrees in the diagonal direction of the pupil (in a reciprocating optical path in which the light is transmitted through the objective lens, reflected by the wafer surface and transmitted through the objective lens again). Therefore, the leakage light from the analyzer is transmitted according to the rotation amount, and the pupil image observed by the imaging device 17 becomes bright in the diagonal direction.

Then, the wafer with the pattern having the structural birefringence is set, the aperture shape and aperture position of the field stop 5 or field stop 16 are properly set, and the light specularly reflected from the wafer surface is observed on the pupil while the periodic direction of the pattern of the wafer surface is rotated with respect to the transmission axis of the polarizer. Then, changes in luminance and hue are recognized in the dark portions of the bare wafer.

This is because the light diffracted from the wafer pattern and that specularly reflected from the wafer pattern are observed on the pupil. Particularly, when the aperture shape and aperture position of the field stop 5 or field stop 16 are set in the region where the pattern to be inspected is formed, diffracted light is not observed and changes in luminance and hue appear in the pupil formed in the imaging surface of the imaging device 17. This is because the linearly polarized light with which the wafer is illuminated is reflected in the form of the elliptically polarized light by the structural birefringence, and the elliptically polarized light is transmitted through the analyzer to form the pupil in the imaging surface of the imaging device 17.

For example, the luminance is enhanced in the whole of the pupil image when the wafer pattern period direction is set at the 45° direction and the 135 degree direction with respect to the transmission axis of the polarizer.

When the wafer pattern period direction is set at 22.5 degrees and 67.5 degrees with respect to the transmission axis of the polarizer, it is found that a change in luminance distribution in the pupil with a change in the pattern profile is maximized as described above.

In the luminance distribution in the pupil, changes in luminance and hue are recognized depending on the position in the pupil according to a change in the pattern profile.

The invention claimed is:

1. An apparatus which detects a defect of a repeated pattern formed on a substrate surface of a substrate, the apparatus comprising:
    a stage on which the substrate is placed;
    a light source;
    an objective lens;
    an illumination optical system for epi-illumination of the substrate surface with linearly polarized light, from the light source transmitted through the objective lens;
    an analyzer that is defined by a transmission axis;
    an imaging device which takes a pupil image of the objective lens that is formed with the light of illumination reflected from the substrate surface and transmitted through the objective lens and the analyzer, the transmission axis of the analyzer being set to satisfy a cross-nichols condition along with a direction of vibration of the linearly polarized light; and
    a detecting unit which compares the pupil image to a pupil image of a substrate surface that does not have a defect to detect.

2. An apparatus which detects a defect of a repeated pattern formed on a substrate surface of a substrate, the apparatus comprising:
    a stage on which the substrate is placed;
    a light source;
    an objective lens;
    an illumination optical system for epi-illumination of the substrate surface with linearly polarized light, from the light source transmitted through the objective lens;
    an analyzer that is defined by a transmission axis;
    an imaging device which takes a pupil image of the objective lens that is formed with the light of illumination reflected from the substrate surface and transmitted through the objective lens and the analyzer, the transmission axis of the analyzer being set to satisfy a cross-nichols condition along with a direction of vibration of the linearly polarized light; and
    a detecting unit which compares portions of the pupil image to each other to detect the defect on the substrate, the portions being symmetrical in relation to an optical axis.

3. The apparatus according to claim 1, wherein the illumination optical system includes:
    an illuminance homogenizing unit;
    a plurality of interference filters which can select an arbitrary wavelength band; and
    an aperture stop, and
    illumination for the objective lens is variable.

4. The apparatus according to claim 1, wherein defect detection of the substrate is performed using an area of the detected pupil image where sensitivity of detecting a defect is larger.

5. The apparatus according to claim 1, wherein a plurality of kinds of aperture stops are provided in the illumination optical system such that one of the plurality of kinds of aperture stops can be selected for use.

6. A defect detecting method for detecting a defect of a repeated pattern formed on a substrate surface of a substrate, the defect detecting method comprising:
    epi-illuminating the substrate surface with linearly polarized light, from a light source transmitted through an objective lens;
    obtaining a pupil image of the objective lens by an imaging device, which takes the pupil image formed with the light of illumination reflected from the substrate surface and transmitted through the objective lens and an analyzer, a transmission axis of the analyzer being set to satisfy a cross-nichols condition along with a direction of vibration of the linearly polarized light; and
    comparing the pupil image to a pupil image of a substrate surface that does not have a defect to detect.

7. The defect detecting method according to claim 6, wherein the comparison of the pupil images is a comparison of a luminance distribution in a radial section of the obtained pupil image to a luminance distribution in a radial section of the pupil image of the substrate surface that does not have a defect.

8. The defect detecting method according to claim 6, wherein detection of the defect is performed based on a threshold and a difference between a luminance distribution of the obtained pupil image and a luminance distribution of the pupil image of the substrate surface that does not have a defect.

9. A defect detecting method for detecting a defect on a sample, a repeated pattern formed on a sample surface of the sample, the defect detecting method comprising:
    epi-illuminating the sample surface with linearly polarized light, from a light source transmitted through an objective lens;
    obtaining a pupil image of the objective lens by an imaging device, which takes the pupil image formed with the light of illumination reflected from the sample surface and transmitted through the objective lens and an analyzer, a transmission axis of the analyzer being set to satisfy a cross-nichols condition along with a direction of vibration of the linearly polarized light; and
    comparing portions of the pupil image to each other to detect the defect on the sample, the portions being symmetrical in relation to an optical axis.

10. The defect detecting method according to claim 6, wherein detection of the defect of the substrate is performed using an area of the obtained pupil image where sensitivity of detecting a defect is larger.

11. The defect detecting apparatus according to claim 1, further comprising:
 a pupil imaging optical system which forms the pupil image of the objective lens with light of illumination reflected from the substrate surface and transmitted through the objective lens and the analyzer.

12. The defect detecting apparatus according to claim 2, further comprising:
 a pupil imaging optical system which forms the pupil image of the objective lens with light of illumination reflected from the substrate surface and transmitted through the objective lens and the analyzer.

13. The defect detecting apparatus according to claim 1, wherein
 the illumination system is configured such that a pupil plane of the objective lens is positioned between a half mirror and the objective lens.

14. The apparatus according to claim 1, further comprising:
 a polarizer which transmits light from the light source and changes the light into the linearly polarized light.

15. The apparatus according to claim 2, further comprising:
 a polarizer which transmits light from the light source and changes the light into the linearly polarized light.

16. The defect detecting method according to claim 6, further comprising:
 transmitting light from the light source through a polarizer to change the light into the linearly polarized light.

17. The defect detecting method according to claim 9, further comprising:
 transmitting light from the light source through a polarizer to change the light into the linearly polarized light.

18. The defect detecting method according to claim 16, wherein a repetition direction of the repeated pattern is set to a direction rotated by 45° from a direction of the polarizer.

19. The defect detecting method according to claim 16, wherein a repetition direction of the repeated pattern is set to a direction rotated by 22.5° or 67.5° from a direction of the polarizer.

* * * * *